United States Patent [19]

Setter et al.

[11] Patent Number: 4,865,717
[45] Date of Patent: Sep. 12, 1989

[54] ELECTROCHEMICAL MICRO SENSOR

[75] Inventors: Joseph R. Setter, Naperville; G. Jordan Maclay, Maywood, both of Ill.

[73] Assignee: Transducer Research, Inc., Naperville, Ill.

[21] Appl. No.: 230,684

[22] Filed: Aug. 10, 1988

Related U.S. Application Data

[63] Continuation-in-part of Ser. No. 53,705, May 26, 1987, abandoned.

[51] Int. Cl.$^4$ .............................................. G01N 27/56
[52] U.S. Cl. .................................. 204/412; 204/415; 204/425; 204/426
[58] Field of Search ................ 204/415, 425, 426, 412

[56] References Cited

U.S. PATENT DOCUMENTS

| 751,897 | 2/1904 | Bodländer | 436/100 |
|---|---|---|---|
| 2,913,386 | 11/1959 | Clark | 204/415 |
| 3,260,656 | 7/1966 | Ross | 204/1 T |
| 3,305,457 | 2/1967 | Hyman | 204/1 T |
| 3,701,632 | 10/1972 | Lovelock | 436/151 |
| 3,764,269 | 10/1973 | Oldham et al. | 422/83 |
| 3,776,832 | 12/1973 | Oswin et al. | 204/411 |
| 3,824,168 | 7/1974 | Oswin et al. | 204/411 |
| 3,836,449 | 9/1974 | Lovelock | 204/277 |
| 3,909,386 | 9/1975 | Oswin et al. | 204/408 |
| 4,076,596 | 2/1978 | Connery et al. | 204/1 T |
| 4,169,779 | 10/1979 | Tataria et al. | 204/412 |
| 4,184,937 | 1/1980 | Tataria et al. | 204/412 |
| 4,227,984 | 10/1980 | Dempsey et al. | 204/408 |
| 4,228,400 | 10/1980 | Bruckenstein et al. | 324/450 |
| 4,267,023 | 5/1981 | Frant et al. | 204/1 T |
| 4,298,573 | 11/1981 | Fujishiro et al. | 422/94 |
| 4,303,612 | 12/1981 | Sonley | 422/94 |
| 4,304,652 | 12/1981 | Chiba et al. | 204/425 |
| 4,329,214 | 5/1982 | Spritzer et al. | 204/431 |
| 4,346,585 | 8/1982 | Yasuda et al. | 73/23 |
| 4,347,732 | 9/1982 | Leary | 73/23 |
| 4,387,165 | 6/1983 | Youngblood | 436/121 |
| 4,406,770 | 9/1983 | Chan et al. | 204/406 |
| 4,423,407 | 12/1983 | Zuckerman | 338/34 |
| 4,462,890 | 7/1984 | Touda et al. | 204/425 |
| 4,477,541 | 10/1984 | Fraioli | 429/33 |
| 4,563,249 | 1/1986 | Hale | 204/1 T |
| 4,571,292 | 2/1986 | Liu et al. | 204/412 |
| 4,587,003 | 5/1986 | Tantram et al. | 204/412 |
| 4,587,105 | 5/1986 | Bonne et al. | 422/98 |
| 4,591,414 | 5/1986 | Zaromb et al. | 204/1 T |

Primary Examiner—G. L. Kaplan
Attorney, Agent, or Firm—Larson & Taylor

[57] ABSTRACT

A micro-amperometric electrochemical sensor for detecting the presence of a pre-determined species in a fluid material is disclosed. The sensor includes a smooth substrate having a thin coating of solid electrolytic material deposited thereon. The working and counter electrodes are deposited on the surface of the solid electrolytic material and adhere thereto. Electrical leads connect the working and counter electrodes to a potential source and an apparatus for measuring the change in an electrical signal caused by the electrochemical oxidation or reduction of the species. Alternatively, the sensor may be fabricated in a sandwich structure and also may be cylindrical, spherical or other shapes.

20 Claims, 4 Drawing Sheets

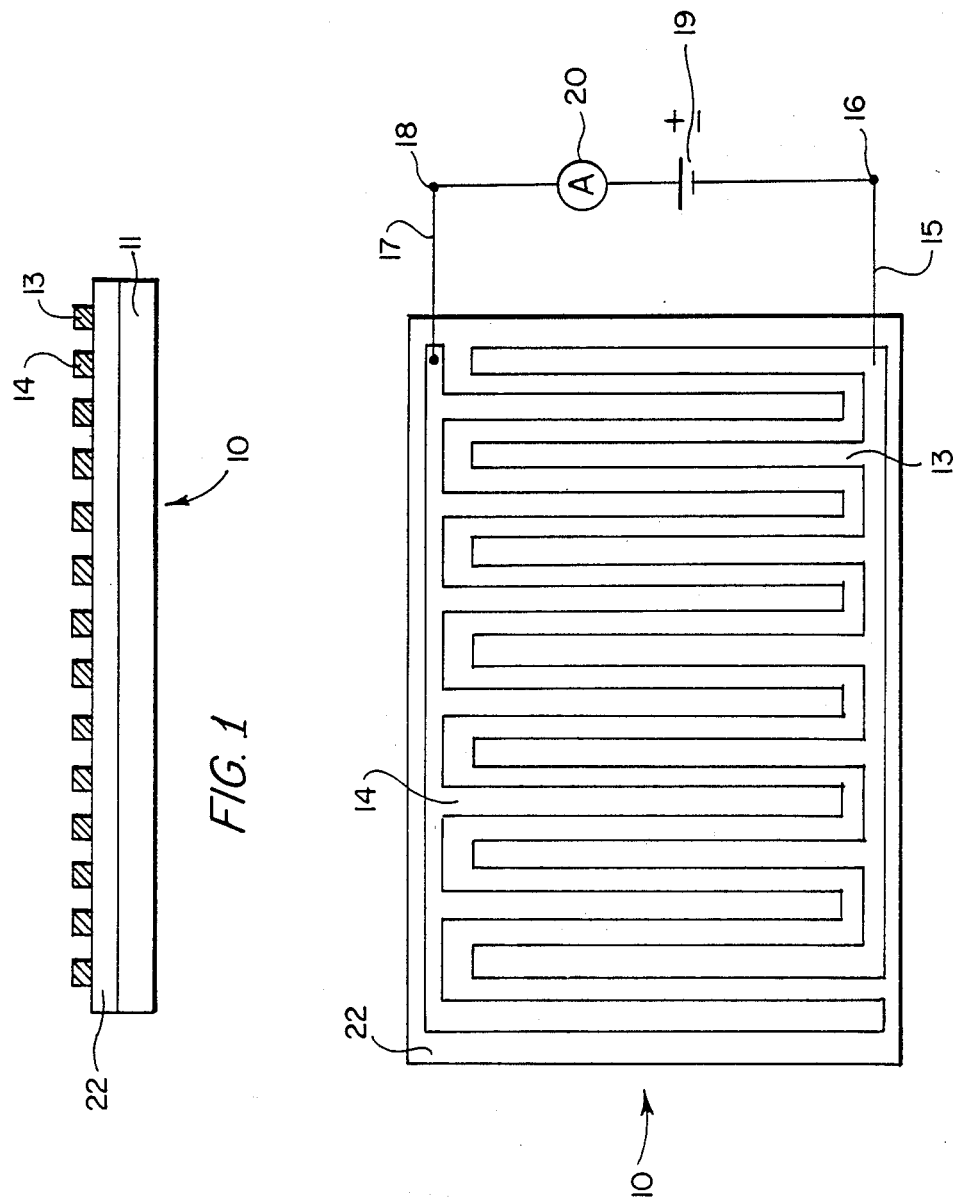

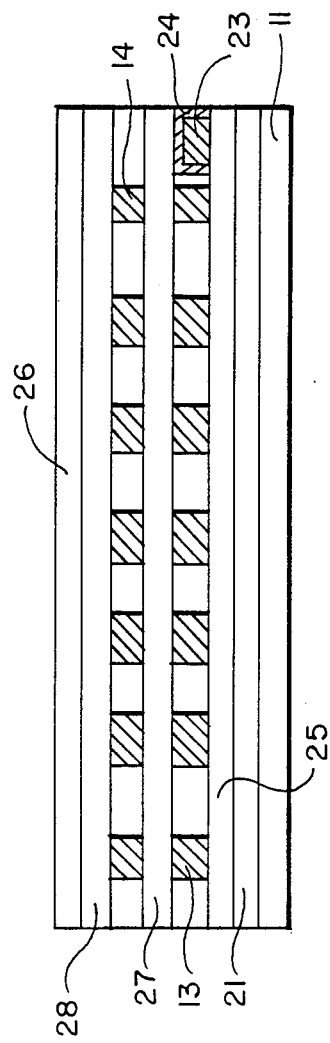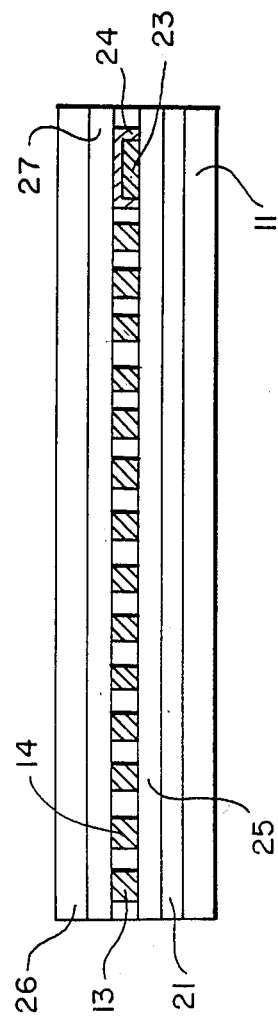
FIG. 4
FIG. 3

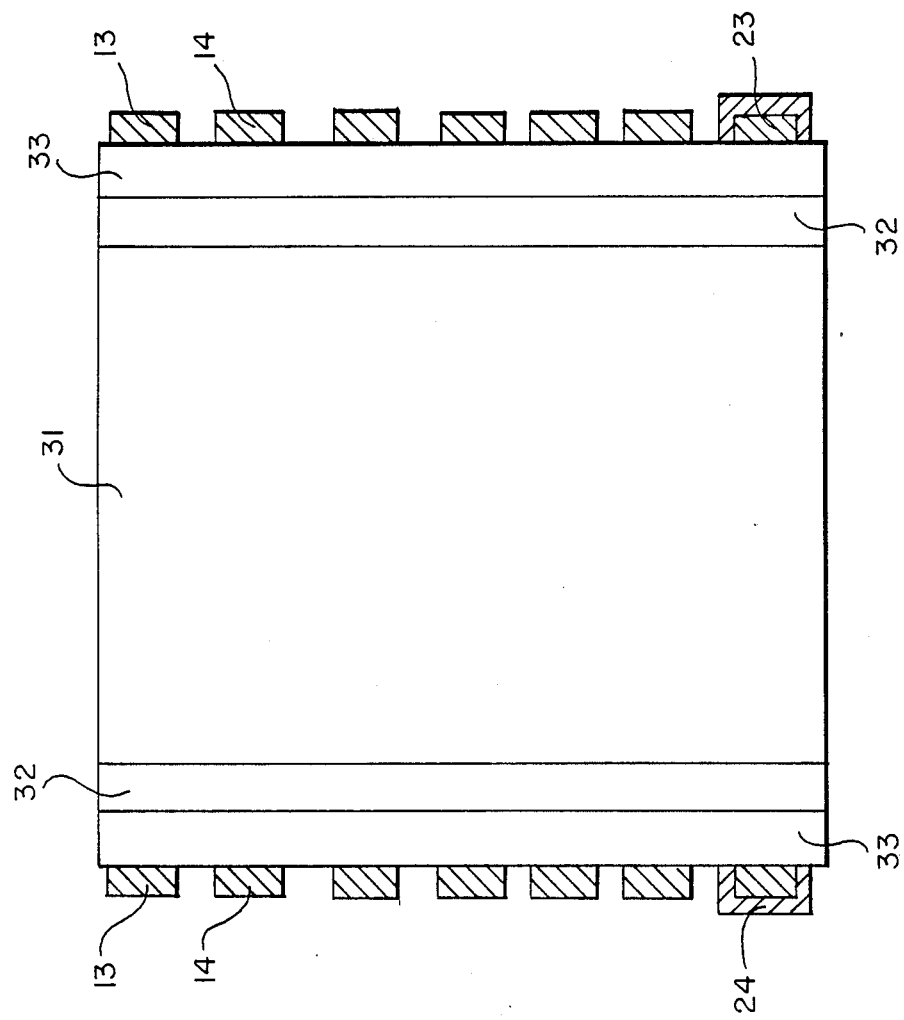

to the electrodes. Whereas the Ross cell effectively overcomes the problems of alteration of the electrodes and/or electrolyte, depletion of the species from the test fluid, and extension of the depletion layer into the test fluid causing stirring and fouling dependence, certain other shortcomings are still evident. Among them is the fact that readings with the Ross-type cell, obtained by measuring the current flow between the electrodes, tend to stablize within a maximum of one minute in accordance with the Ross patent.

ELECTROCHEMICAL MICRO SENSOR

This invention was made with Government support under contract number ANL-61892401 awarded by the Department of Energy. The Government has certain rights in this invention.

This application is a continuation-in-part of application Ser. No. 053,705 filed May 26, 1987, now abandoned.

FIELD OF THE INVENTION

The invention relates to electrochemical apparatus for sensing the presence of a species in a fluid material. More particularly the invention relates to an improved apparatus for generating an electric signal in response the the presence of a predetermined species in a fluid material.

BACKGROUND OF THE INVENTION

Electrochemical sensors for the detection of the presence of a species in a fluid material have existed for quite some time. Such sensors include the Clark cell described in U.S. Pat. No. 2,913,386 issued Nov. 17, 1959. The apparatus disclosed in that patent utilizes a dual electrode structure immersed in an electrolyte and encased at least in part in a membrane which is permeable to a predetermined species. In operation such a device allows the permeation of the species to be detected through the membrane and reduces said species at the cathode. At the same time the anode is oxidized as a results of the electrical and ionic connections between the anode and cathode. These oxidation and reduction reactions generate a current which is measurable and is proportional to the concentration of the species being detected. The Clark cell is a large bulky apparatus and must include a liquid electrolytic medium in which the electrodes are immersed. The Clark apparatus suffers from several disadvantages including consumption of the species being detected during detection, slow response times and alteration of the electrolyte during detection Some of the above-mentioned disadvantages of the Clark-type electrode cell are avoided by apparatus of the type described in U.S. Pat. No. 3,260,656 issued on July 12, 1966 to James W. Ross, Jr. The Ross apparatus utilizes a sandwich comprising a cathode and an anode with a spacer therebetween. This sandwich is immersed in an electrolyte and is geometrically oriented so that the electrodes are parallel to a membrane which is permeable to the species being measured. The membrane combines with a housing to enclose the cathode-anode combination in an electrolyte. In the Ross-type cell the species being measured is consumed at one electrode and regenerated at the other electrode such that no net consumption of the species being detected occurs. Therefore the Ross sensor does not consume the species being measured as a result of the electrochemical reaction of that species with the electrodes. Whereas the Ross cell effectively overcomes the problems of alteration of the electrodes and/or electrolyte, depletion of the species from the test fluid, and extension of the depletion layer into the test fluid causing stirring and fouling dependence, certain other shortcomings are still evident. Among them is the fact that readings with the Ross-type cell, obtained by measuring the current flow between the electrodes, tend to stablize within a maximum of one minute in accordance with the Ross patent. It has been found that response times of this order are not suitable for many applications. A further disadvantage is that the diffusion layer thickness in the Ross cell is determined by the interelectrode distance which is subject to variation as the assembly is stressed by forces arising from temperature and/or pressure variations. Yet another disadvantage is the cumbersome nature of the layered structure making reliable fabrication of Ross-type devices difficult.

Yet another apparatus for electrolytically detecting a species in a fluid is described in U.S. Pat. No. 4,076,596 issued to Connery et al. on Feb. 28, 1978. The apparatus of Connery et al. includes an insulating substrate and a plurality of fingerlike electrodes deposited on the surface of the substrate in a closely spaced interleaved geometric pattern. The electrodes are covered with a thin film of electrolyte and a permeable membrane. The electrolyte is selected so that the species being measured is generated at one electrode and consumed at the other with no net consumption of the species being detected. The Connery et al. apparatus may include a solid electrolyte deposited on the electrodes. While the Connery et al. apparatus eliminates some of the problems of the Ross-type cell it has several disadvantages of its own. One primary disadvantage of the Connery et al. apparatus is that the solid electrolyte is deposited on top of the electrodes. The electrodes form an irregular surface having high points where the electrodes are present and valleys at the spaces between the electrodes. This makes it difficult to deposit a solid electrolyte coating which will be smooth, consistent, homogeneous and adhere to the electrodes. In addition, the coating of electrolyte will be distorted by changes in humidity and temperature because of the irregular surface upon which it is coated. Another problem with the Connery et al. apparatus is that its response times may be too slow for some applications. This results because of the electrolytic resistance of the electrolyte which forms a barrier between the electrodes and the test fluid. As a result, the species must diffuse through the electrolyte prior to contacting the electrodes. Since the Connery et al. electrolyte is coated onto an irregular surface the electrolyte must be thicker than if it were coated on a flat surface to accomplish a complete coating. Accordingly the electrolytic resistance will be lower but diffusion will be slower and can significantly slow response times.

It is the primary object of the present invention to provide an apparatus for electrolytically detecting a species in a fluid material, which has smooth electrolyte coatings with good repeatability.

It is a further object of the present invention to provide a solid electrolyte layer having excellent adherence to the electrodes.

It is a still further object of the present invention to provide a thinner electrolyte layer to thereby reduce the diffusion resistance of the apparatus.

It is a still further object of the present invention to provide an apparatus having a structure which minimizes stresses on the electrolyte and thereby decreases distortion of the electrolyte as a result of temperature and/or humidity variations.

It is a still further object of the present invention to provide an apparatus for electrolytically detecting a species in a fluid material which is capable of operating at room temperature or temperatures significantly lower than prior art electrochemical sensors.

It is a still further object of the present invention to provide an apparatus for electrolytically detecting a species in a fluid material with a response time which is fast enough for use in applications requiring a very fast response.

These and other objects of the present invention will be apparent to one of ordinary skill in the art from the summary and detailed descriptions which follow.

SUMMARY OF THE INVENTION

The present invention relates to a solid electrochemical sensor for generating an electrical signal in response to contact with a predetermined species present in a fluid material comprising a substrate having at least one surface, a solid electrolytic medium having first and second surfaces, said first surface of said medium being in contact with and adhering to said at least one surface of said substrate, a working electrode means in contact with and adhering to said second surface of said medium, an electrical power source connected for biasing said working electrode means at a potential at which said species will be consumed at said working electrode, and a counter electrode means in contact with and adhering to said second surface of said medium and being connected to said power source for completing a circuit in which a current is capable of flowing through both of said electrode means as a result of the electrochemical reaction occurring at said working electrode means.

A second embodiment of the invention relates to a solid electrochemical sensor for generating an electrical signal in response to contact with a predetermined species present in a fluid material comprising a substrate having at least one surface, a first layer of a solid electrolytic medium having first and second surfaces, said first surface of said first layer of medium being in contact with and adhering to said at least one surface of said substrate, a counter electrode means in contact with and adhering to said second surface of said first layer of electrolytic medium, a second layer of a solid electrolytic medium having first and second surfaces, said first surface of said second layer of medium being in contact with and adhering to said counter electrode means, a working electrode means in contact with and adhering to said second surface of said second layer of electrolytic medium, an electrical power source connected for biasing said working electrode means at a potential at which said species will be consumed at said working electrode, and means for connecting said counter electrode means to said power source for completing a circuit in which a current is capable of flowing through both of said electrode means as a result of the electrochemical reaction occurring at said working electrode means.

BRIEF DESCRIPTION OF THE DRAWINGS

FIG. 1 is a cross-sectional view of the amperometric electrochemical apparatus of the present invention.

FIG. 2 is a top plan view of the amperometric electrochemical sensing apparatus of the present invention.

FIG. 3 is a cross-sectional view of an alternate embodiment of the amperometric electrochemical sensing apparatus of the present invention.

FIG. 4 is a cross-sectional view of a sandwich-type amperometric electrochemical sensing apparatus in accordance with the present invention.

FIG. 5 is a cross-sectional view of a cylindrical amperometric electrochemical sensing apparatus in accordance with the present invention.

DETAILED DESCRIPTION OF THE PREFERRED EMBODIMENTS

Figure 6:
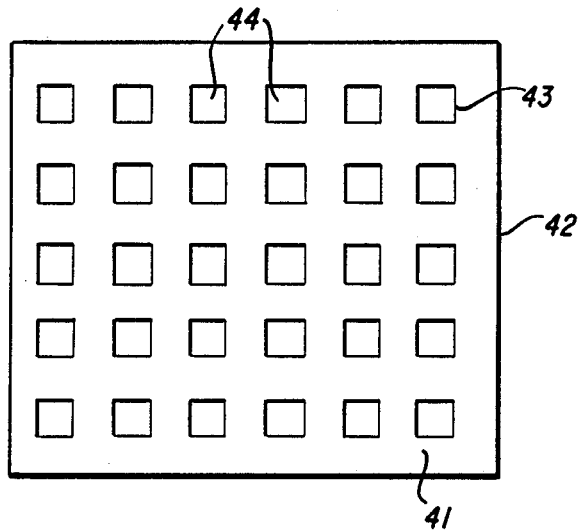
FIG. 6 is a plan view of a grid pattern electrode in accordance with the present invention.

Referring now to FIG. 1 there is shown an electrochemical sensing apparatus 10 including a substrate 11, an electrolyte 22, a counter electrode means 13 and a working electrode means 14. The sensor depicted in FIG. 1 is the simplest, least expensive, as well as one of the most efficient sensors in accordance with the present invention.

Referring now to FIG. 2 which is a top plan view of the apparatus of FIG. 1 showing the fingerlike projections of the electrodes 13 and 14. Counter electrode 13 is connected by way of line 15 to terminal 16 and the working electrode 14 is connected by line 17 to the terminal 18. The electrical circuit also includes a series connected electrical power source 19 for biasing the working electrode means 14 at a desired potential and an ammeter 20.

Referring now to FIG. 3 there is shown an alternate embodiment of the electrochemical sensor of the present invention. The sensor depicted in FIG. 3 includes substrate 11 having an oxide layer 21 on the surface thereof. Deposited on the oxide layer 21 and adhering to the oxide layer 21 is a first layer 25 of electrolytic medium. Deposited on the first layer 25 of electrolytic medium are the counter electrode means 13 and the working electrode means 14. Also deposited on the first layer 25 of electrolytic medium is a reference electrode 23 having a protective coating 24 thereon. Deposited on top of the electrodes 13, 14 and the protective coating 24 is a second layer 27 of electrolytic medium. Finally, on top of the second layer 27 of electrolytic medium is shown a selectively permeable membrane 26.

Referring now to FIG. 4 there is depicted another alternative embodiment of the present invention wherein the electrochemical sensing means is formed in a sandwich-type structure. This sandwich-type structure is built on a layer of substrate 11. The layer of substrate 11 includes an oxide layer 21 on the surface thereof. Deposited on top of the oxide layer 21 is a first layer 25 of electrolytic medium. Deposited on the first layer 25 of electrolytic medium is the counter electrode means 13 and the reference electrode 23. The reference electrode 23 is coated by a protective coating 24. Deposited on top of the counter electrode 13 and protective coating 24 is a second layer 27 of electrolytic medium. Then, deposited on the second layer 27 of electrolytic medium is the working electrode 14 of the electrochemical sensor. Deposited on top of the working electrode means 14 is a third layer 28 of electrolytic medium which includes a selectively permeable membrane 26 thereon.

Referring now to FIG. 5 there is shown yet another alternate embodiment of the present invention. FIG. 5 depicts a cross-sectional view of a cylindrical electrochemical sensor in accordance with the present invention. The cylindrical electrochemical sensor includes a substrate 31 having an oxide layer 32 on the surface thereof. On top of the oxide layer 32 is deposited a first layer 33 of electrolytic medium. On the first layer 33 of electrolytic medium is deposited a counter electrode means 13, a working electrode means 14 and a reference electrode 23. The reference electrode 23 is coated with a protective coating 24. It will be understood that any of the alternate embodiments shown in FIGS. 1–4 may be adapted to the cylindrical-shaped electrochemical sensor as well as other possible shapes such as spherical. These alternate shapes may be desirable for specific applications of the sensing device.

The substrate 11 may be made of any suitable materials to which the electrolytic medium can be adhered. The substrate 11 is preferably an insulating material such as glass, quartz, ceramics such as alumina, etc. and silicon. The substrate 11 should have a thickness sufficient to assure the structural integrity of the sensor. Another important feature of the substrate 11 is that it be capable of adhering or being made to ahere to a coating material such as those used to fabricate electrodes and electrolytes. This is important because the electrodes and electrolytes must adhere to the substrate 11. There are several ways to promote adherence of a coating material to the substrate 11. One method involves oxidation of the surface of the substrate 11 to form an oxide layer thereon. Many electrolytic materials adhere well to oxides. An additional oxide layer may also be coated on the surface of the substrate 11 to promote adherence of an electrolyte thereto. Also, adhesion promotors for improving adhesion of Nafion to glass and other siliceous substrates may be used. Such adhesion promoters include but are not limited to N-(trimethoxysilylpropyl)-N,N,N-timethyl-ammonium chloride, octadecyltrichlorosilane, and 8-hydroxy-1,3,6-pyrenetrisulfonic acid trisodium salt. These adhesion promoters chemically bond the electrolyte to the substrate 11 to give additional bonding strength. The adhesion promoters are applied to the substrate 11 just prior to spin coating of the electrolyte onto the substrate. Such promoters are described in Szentirmay, M. N., Campbell, L. F., and Martin, C. R., *Silane Coupling Agents for Attaching Nafion to Glass and Silica*, Anal. Chem., Vol. 58 pp. 661–662, March 1986, which is hereby incorporated by reference.

As mentioned previously, the substrate 11 preferably includes an oxide layer on 21 on the surface thereof to promote the adherence of the electrolytic medium to the substrate 11. Such an oxide layer 21 may be created by simple oxidation of the surface of the substrate 11. For instance, a substrate 11 such as silicon can be surface oxidized to produce a silicon dioxide surface coating. Alternatively, the oxide layer 21 may be deposited on or attached to the surface of the substrate 11 in any suitable manner.

The substrate 11 should have a smooth surface before and after oxidation. Such a smooth surface will promote smooth coatings of electrolytic medium on the substrate 11. Moreover, a smooth surface will lead to consistent and repeatable coatings of electrolytic medium enabling mass production of consistent sensors. Further, the smooth surface of the substrate 11 promotes adhesion of the electrolytic medium to the substrate and thereby prevents the electrolytic medium from peeling off the substrate 11. Finally, the existence of a smooth surface on the substrate 11 minimizes the stresses applied to the electrolytic medium by the substrate 11 upon exposure to varying temperatures and/or humidity conditions. This, in turn, will minimize the distortion of the electrolytic medium as a result of these temperature and/or humidity variations.

The electrolytic medium of the present invention is preferably a solid material. The electrolytic medium must be capable of allowing diffusion of all reactants and products between the cathodes and anodes as well as allowing exchange of the measured species with the test fluid. The electrolytic medium must also have satisfactory chemical, thermal and dimensional stability. Such polymer electrolytes such as poly-sulfonic acids, typically polystrene sulfonic acid or perfluoro linear polymers such as those marketed under the name "Nafion" by Du Pont are suitable for use as the electrolytic medium of the present invention. In addition, the electrolytic medium must be capable of adhering not only to the substrate 11, but also to the electrodes 13, 14 or the electrolytic medium must be capable of being adhered to the substrate 11 and the electrodes 13, 14 by adhesives, adhesion promoters or the like.

Electrolytes of the type employed in the electrolytic medium of present invention demonstrate excellent electrolytic and electronic compatibility with oxides such as silicon dioxide. As a result, it is preferable to coat such electrolytes onto an oxide covered surface. The oxide layer 21 can be obtained by thermal oxidation of the semiconductor wafer substrate 11. Other substrates 11 that are already oxides may also be used, such as alumina, sapphire, glass and polymers. In order to obtain smooth, repeatable layers of electrolytic medium, the electrolyte may be spin coated onto the surface of the substrate 11. This process is described in our co-pending application Serial No. 053,722, filed on May 26, 1987 and now Patent No. 4,795,543. This spin coating technique produces a very thin, smooth and homogeneous coating of the electrolytic medium on the substrate 11. Other methods of coating the electrolytic medium onto the substrate 11 may be used if they produce a coating having the desired properties of smoothness, homogeneity, thickness and structural stability.

The electrodes of the present invention are preferably metal. These electrodes may be deposited on the surface of the electrolytic medium through the use of thick film, or thin film techniques. Such methods include sputtering and/or evaporation onto the electrolytic surface of a thin film of metal to form the electrodes with the definition of the surface areas being accomplished by photo-etching processes. Other thin film techniques such as deposition of a metal layer and photo-etching of that layer are also acceptable.

The metals used to fabricate the electrodes of the present invention may include one or more of the following: platinum, palladium, rhodium, lead, silver, gold and iridium. It will be understood that other materials may be used as long as they satisfy the requirements of the present invention. These other materials must be capable of reacting with the species to be detected, as well as adhering or being adhered to the electrolytic medium. Selection of the proper electrode material for a particular reaction will depend on the species which is to be detected, as well as the ability to adhere the electrode material to the electrolytic medium.

The analysis or identification of a gas using these electrodes may be accomplished in any of a number of ways. For instance, such electronic variables as resistance, impedance, electrolytic reactions, oxidation-reduction reactions and polarization may be monitored during exposure of the sensor to a gas. Data obtained by monitoring any of these electronic variables can be used to analyze or identify a gas or components thereof.

The electrodes may be characterized as a working electrode 14, a counter electrode 13 and a reference electrode 23. The working electrode 14 is the electrode at which the species is consumed by an electrochemical reaction. The counter electrode 13 is the electrode at which the species being detected is preferably regenerated by an electrochemical reaction. However, counter electrodes 13 which do not regenerate the species being detected, such as those of a Clark cell may also be used though they are not preferred. The reference electrode 23 does not participate in the chemical reactions but does serve to provide a potential reference for the working electrode 14. Normally, a potential is applied between the reference electrode 32 and the working electrode 14.

Since it is often desirable to prevent electrochemical reaction from occurring at the reference electrode 23, the reference electrode 23 is often coated to prevent exposure of the reference electrode 23 to the species. Such coatings may include epoxies and any other coatings which do not allow the diffusion of the species to the surface of the reference electrode 23. Alternatively, the reference electrode 23 may be left uncoated and thereby be exposed to the species. In this instance it is necessary to include a correction factor in the system monitoring means in order to compensate for the electrochemical reaction occurring at the reference electrode 23. The reaction occurring at the reference electrode 23 will cause a change in potential between the reference electrode 23 and the working electrode 14. This potential change can be accounted for through the use of the Nernst equation. Therefore, the reference electrode 23 may be left exposed to the species if the monitoring means is programmed to compensate for the change in potential by calculating such change using the Nernst equation.

A preferred embodiment of the present invention also includes a selectively permeable membrane 26 which may be deposited over the top of the electrodes 13, 14 or over the top of a second layer of electrolytic medium. This selectively permeable membrane 26 serves to allow the diffusion of the species to be detected through to the working electrode 14 and the electrolytic medium. However, it does not allow diffusion of certain other materials which may be present in the fluid material being sensed. Therefore, the membrane 26 can be used to improve species specificity of the sensing apparatus. The membrane 26 can also be used to prevent harmful components of the fluid material from reaching the electrodes 13, 14 and the electrolytic medium and altering their properties in some way. The membrane 26 may be composed of any material which is selectively permeable to the species being detected. Such materials include rubbers and synthetic polymers among other materials.

FIGS. 1-3 depict a planar sensor structure in accordance with the present invention. Such a planar structure is the most preferred embodiment since it requires the least number of components, minimizes the electrolytic interference and simplifies the construction. Further, the planar sensor allows for smoother and more homogeneous coatings of the electrolytic medium since these coatings, with the exception of the second layer of electrolytic material in FIG. 3, are being applied to smooth surfaces. This type of sensor geometry gives excellent results because of its simplicity of design, ease of manufacture, and consistency.

The device of FIGS. 1 and 2 offers many advantages over prior art devices. In this embodiment the electrodes 13 and 14 are in direct contact with the fluid material thereby eliminating the need for the fluid material to diffuse across membranes or electrolytes. This direct contact results in a shorter response time because of the elimination of the diffusion resistance of electrolytic or membrane layers. Another important advantage of this embodiment results from the coating of the electrolytic medium directly onto the substrate 11 rather than onto the electrodes 13 and 14. Since the substrate 11 has a smooth surface the electrolytic medium will form a smooth, thin, homogeneous coating on the substrate 11. Prior art devices coated on the electrolytic medium over the electrodes 13, 14 thus forming a nonhomogeneous coating due to the roughness of the surface onto which the electrolytic medium had to be coated. The coating of the invention also minimizes the stresses placed on the electrolyte by the surface onto which it is coated since the electrolytic medium is coated onto a smooth surface.

Another embodiment of the present invention is shown in FIG. 4. This sensor has a sandwich-type structure. Again, there is a thin coating of a first layer 25 of electrolytic medium between the substrate 11 and the counter electrode means 13. However, in the sandwich-type structure there is also a second layer 27 of electrolytic medium coated atop the counter electrode means 13. The sandwich-type structure has several advantages over the planar structure. The main advantage of the sandwich-type structure is the increased rigidity of the sensor structure due to the extra layers of material applied thereto. This increased rigidity will minimize the distortion of the electrodes 13 and 14 and electrolytic medium which usually results from thermal and physical stresses placed on the sensor apparatus. Another advantage of the sandwich-type structure is that the counter electrode 13 and reference electrode 23 are partially shielded from the fluid material by an additional layer of electrolytic medium. This will minimize undesirable reactions at the counter electrode 13 and the reference electrode 23. Excellent sandwich structures are possible as a result of the coating techniques developed in our co-pending application Ser. No. 053,722, filed on May 26, 1987 which is hereby incorporated by reference. These coating techniques allow for smooth, relatively homogeneous coatings of the electrolytic medium to be applied over the electrodes 13, 14.

In the preferred embodiment of the present invention, the perimeter of the working electrode 14 is maximized with respect to the area of contact of the working electrode 14 with the electrolytic medium. This maximization of the perimeter to area ratio results in a corresponding maximization of the signal to noise ratio of the sensor. The theoretical basis for this result is that the area of contact between the working electrode 14 and the electrolytic medium appears to be responsible for the noise in the sensor. Whereas, the electrochemical reaction between the working electrode 14 and the species appears to be catalyzed by the electrolytic medium. Therefore, the triple-phase boundary between the working electrode 14, electrolytic medium, and the species is the preferred location for the electrochemical reaction between the species and the working electrode 14. As a result, the signal generated by the electrochemical reaction appears to be directly proportional to the perimeter of the working electrode 14 since the perimeter is a measure of the triple-phase boundary. The preferred perimeter to area ratio (perimeter$^2$/area) is from about 0.4 to 500 and more preferably is from about 2 to about 500.

When the electrodes are located atop the electrolyte, the most desirable electrode geometry is long, thin electrodes whereby the surface area of the electrode in contact with the electrolyte is minimized while the triple-phase boundary at the electrode edges in contact with the electrolyte is maximized. Thus, the optimum configuration for a rectangular electrode occurs when one side is much longer than the other side, in which rectangular electrode the perimeter to area ratio and signal to noise ratio is proportional to the ratio of the sides of the rectangle, which is much greater than 1. When the electrolyte is coated over the surface of the electrodes, the length, width and height all become important to the perimeter to area ratio. Accordingly, in three dimensions it is highly advantageous to maximize one dimension of the electrode while minimizing the other two dimensions to thereby obtain the greatest perimeter to area ratio.

Referring now to FIG. 6, there is shown an electrode configuration which may be adopted in order to maximize the perimeter to area ratio. It should be noted that these type of grid pattern electrodes provide a high perimeter to area ratio since both the external perimeter 42 of the electrode 41 and the internal perimeter 43 around the holes 44 of the electrode 41 both contribute to the signal strength of the electrode. Further, when employing the grid pattern, the holes in the electrode serve to help minimize the area of the electrode in contact with the electrolyte and thus minimize the background noise created by the surface area contact of the electrode with the electrolyte. The geometry shown in FIG. 6 is the preferred embodiment for obtaining a high and beneficial signal to noise ratio from these microfabricated electrode structures having the electrolyte coated atop the electrodes.

These grid electrodes are easily fabricated by etching uniformly spaced parallel rectangles onto thin copper foil masks. Then, the masks are used to evaporate gold electrodes. A first evaporation of 3500 angstroms of gold is done using the masks and then the masks are rotated 90° and a second evaporation of 3500 angstroms of gold is performed to obtain working electrodes in a grid pattern as shown in FIG. 6.

The preferred grid width is less than 125 micrometers. The preferred grid spacing is less than 200 micrometers. Finally, the preferred number of holes in the grid is greater than 300. These values are somewhat limited by the available microfabrication techniques and improvements in the act of microfabrication should provide the capability of fabricating electrodes having smaller grid widths and grid spacing and larger numbers of holes in these grid pattern electrodes.

It is important to note that the sensing apparatus of the present invention, if it uses a Nafion electrolyte, must be operated in an environment having at least some humidity. The absence of water in the environment will prevent the successful operation of the apparatus by hindering the role of the electrolytic medium. This is because the per fluoro membrane requires water to activate free protons. Other solid electrolytes, such as polyvinylalcohol and polyethylene oxide, may not require the presence of humidity.

One of the primary advantages of the micro sensor of the present invention is that it is capable of operation at much lower temperatures than prior art sensor devices. This device is capable of operating at temperatures of from about −40° to about 300° C. and more preferably the device is operated at between −5° C. and 100° C. The most preferred operating temperatures for the device are from about −5° C. to about 35° C. No heating means is required to operate the sensor since it can be operated at room temperature if desired. Many materials can be used as substrates and membranes over the electrolytes which could not be used in the prior art since extremely high temperature operation is not required for operation of the microsensors of this invention. Thus, the electrolytic medium of the present invention is characterized by the capability to conduct ions in sufficient quantity at room temperature to allow operation of the microsensor at lower temperatures than were possible with prior art microsensors.

In operation, the assembly is contacted with a fluid material including the species to be detected. the species will diffuse to the working electrode 14 and there an electrochemical reaction will take place generating a measurable signal. The signal is measured by the ammeter 20 and the measured signal is preferably fed to a microcomputer for normalization of the signal as well as any other mathematical manipulations such as calibration which may be necessary. The response time for the sensor is usually less than five seconds.

The following examples are provided to illustrate certain embodiments of the present invention.

EXAMPLE 1

A 2" silicon wafer was oxidized to provide an insulating silicon dioxide surface. Then the wafer was spin-coated with a 5% Nafion solution (Aldrich Chemical Co., Milwaukee, Wis.) to make a planar electrolytic structure. A two-step evaporation procedure was used to create grid electrode patterns on the surface of the Nafion layer. An evaporation system containing both e-beam and thermal evaporation capability was used to deposit the electrode structures. A photolithographically etched evaporation mask was prepared from thin copper foil in which a number of parallel rectangles were etched, each 6 mm long and 125 microns wide. After the first evaporation deposition the mask was rotated 90° and a second evaporation was performed. Gold wire (99.9%, Englehard Minerals and Chemicals Co., N.J.) was used as the evaporation source. The electrodes were electrically connected to a power source.

EXAMPLE 2

A sensor fabricated as in Example 1 was exposed to various gas mixtures at a room temperature of about 70°–75° F. with the following results. The sensor was operated at a constant potential of +300 millivolts versus the Platinum/air reference electrode. S/N is the signal to noise ratio of the sensor. The signals are given as normalized values with the signal for $H_2S$ being taken as 1.0 and all other responses being scaled accordingly.

SENSOR SIGNAL TO VARIOUS GAS MIXTURES

| Gas Mixture | Day | Signal (S) | Noise (N) | S/N |
|---|---|---|---|---|
| 92 ppm $NO/NO_2$ | 1 | 2.38 | 0.28 | 8.5 |
| 83 ppm $H_2S/N_2$ | 1 | 27.1 | 0.28 | 27.1 |
| 92 ppm $NO/NO_2$ | 21 | 0.24 | 0.02 | 12.0 |
| 83 ppm $H_2S/N_2$ | 21 | 2.72 | 0.02 | 13.6 |
| 49 ppm $NO_2$/air | 21 | 0.02 | 0.02 | 1.0 |
| 80 ppm $SO_2$/air | 21 | 0.036 | 0.02 | 1.8 |
| 200 ppm CO/air | 21 | 0.00 | 0.02 | 0.0 |
| 100 ppm HCN/air | 21 | spike | 0.02 | spike |

The foregoing description of embodiments of the invention has been presented for purposes of illustration and description. It is not intended to be exhaustive or to limit the invention to the precise forms disclosed, and many modifications and variations will be obvious to one of ordinary skill in the art in light of the above teachings. Accordingly, the scope of the invention is to be defined by the claims appended hereto.

What is claimed is:

1. A solid electrochemical sensor which operates at temperatures below 300° C. for generating an electrical signal in response to contact with a pre-determined species present in a fluid material comprising:
    a substrate having at least one surface,
    a solid electrolytic medium having sufficient ionic conductivity at temperatures below 100° C. to sustain an ionic current flow and having first and second surfaces, said first surface of said medium being in contact with and adhering to said at least one surface of said substrate,
    a working electrode means in contact with and adhering to said second surface of said medium,
    an electrical power source connected for biasing said working electrode means at a potential at which said species will be consumed at said working electrode means, and
    a counter electrode means in contact with and adhering to said second surface of said medium and being connected to said power source for completing a circuit in which a current is capable of flowing through both of said electrode means as a result of the electrochemical reaction occurring at said first working electrode means.

2. An apparatus in accordance with claim 1 further comprising a reference electrode having at least one surface in contact with and adhering to said second surface of said medium.

3. An apparatus in accordance with claim 2 further comprising a coating over said reference electrode to prevent exposure of said reference electrode to said species.

4. An apparatus in accordance with claim 2 further comprising a selectively permeable membrane means separating all of said electrodes means from said fluid material.

5. An apparatus in accordance with claim 1 wherein said substrate comprises an insulating material.

6. An apparatus in accordance with claim 1 wherein said electrolytic medium comprises a layer of between about 0.1 and about 4.0 microns in thickness.

7. An apparatus in accordance with claim 6 wherein said working electrode means comprises thin strips of metal which form a grid pattern having a perimeter$^2$ to area ratio of between 2 and about 500.

8. An apparatus in accordance with claim 1 wherein said substrate comprises an oxide layer on said at least one surface of said substrate.

9. An apparatus in accordance with claim 1 wherein said substrate further comprises at least one adhesion promoter on said at least one surface of said substrate to promote adherence between said electrolytic medium and said substrate.

10. An apparatus in accordance with claim 1 further comprising a second layer of a solid electrolytic medium having a first surface in contact with and adhering to said working and counter electrode means.

11. A solid electrochemical sensor for generating an electrical signal in response to contact with a pre-determined species present in a fluid material comprising
    a substrate comprising an insulating material and having at least one surface,
    a first layer of solid electrolytic medium having first and second surfaces, said first surface of said first layer of said medium being in contact with and adhering to said at least one surface of said substrate,
    a counter electrode means in contact with and adhering to said second surface of said first layer of electrolytic medium,
    a second layer of a solid electrolytic medium having first and second surfaces, said first surface of said second layer of said medium being in contact with and adhering to said counter electrode means,
    a working electrode means in contact with and adhering to said second surface of said second layer of electrolytic medium,
    an electrical power source connected for biasing said working electrode means at a potential at which said species will be consumed at said working electrode means, and means for connecting said counter electrode means to said power source for completing a circuit in which a current is capable of flowing through both of said electrode means as a result of the electrochemical reaction occurring at said working electrode means.

12. An apparatus in accordance with claim 11 further comprising a reference electrode in contact with and adhering to said second surface of said first layer of electrolytic medium.

13. An apparatus in accordance with claim 12 wherein said reference electrode is also in contact with an adhering to said first surface of said second layer of electrolytic medium.

14. An apparatus in accordance with claim 12 wherein said reference electrode further comprises a coating to prevent exposure of said reference electrode to said species.

15. An apparatus in accordance with claim 11 further comprising a third layer of electrolytic medium in contact with and adhering to said working electrode means.

16. An apparatus in accordance with claim 11 further comprising a selectively permeable membrane means separating said working electrode means from said fluid material.

17. An apparatus in accordance with claim 11 wherein said substrate comprises an oxide layer on said at least one surface.

18. An apparatus in accordance with claim 11 wherein said substrate compriss at least one adhesion promoter on said at least one surface of said substrate to promote adherence of said electrolytic medium and said substrate.

19. An apparatus in accordance with claim 11 wherein said working electrode means comprises thin strips of metal which form a grid pattern having has a perimeter$^2$ to area ratio of between about 0.4 and about 500.

20. An apparatus in accordance with claim 11 wherein said first and second layers of electrolytic medium each have a thickness of between about 0.1 and about 4.0 microns.

* * * * *

UNITED STATES PATENT AND TRADEMARK OFFICE
CERTIFICATE OF CORRECTION

PATENT NO. : 4,865,717

DATED : September 12, 1989

INVENTOR(S) : Stetter, et al

It is certified that error appears in the above-identified patent and that said Letters Patent is hereby corrected as shown below:

On the title page:

Inventors name should read --Stetter et al-- not Setter et al.

Inventors: Joseph R. Stetter

Jordan Maclay

Signed and Sealed this

Ninth Day of October, 1990

Attest:

HARRY F. MANBECK, JR.

*Attesting Officer*      *Commissioner of Patents and Trademarks*